United States Patent [19]
Müller et al.

[11] Patent Number: 5,693,831
[45] Date of Patent: Dec. 2, 1997

[54] (2,3-DIHYDRO-5-BENZOFURANYL)-ACETONITRILE

[75] Inventors: Nikolaus Müller, Monheim; Guido Steffan, Odenthal, both of Germany

[73] Assignee: Bayer Aktiengesellschaft, Leverkusen, Germany

[21] Appl. No.: 804,622

[22] Filed: Feb. 27, 1997

[30] Foreign Application Priority Data

Mar. 5, 1996 [DE] Germany ............ 196 08 408.3
Apr. 9, 1996 [DE] Germany ............ 196 14 090.0

[51] Int. Cl.$^6$ ............................................ C07D 307/79
[52] U.S. Cl. ................................. 549/467; 549/469
[58] Field of Search .............................. 549/467, 469

[56] References Cited

PUBLICATIONS

"Antiinflammatory Activity of Some 2,3–Dihydrobenzofuran–5–Acetic Acids and Related Compounds," Hirose et al., *J. Med. Chem.*, 1976, vol. 19, No. 2, pp. 303–308.

*Primary Examiner*—Johann Richter
*Assistant Examiner*—Jane C. Osweckì
*Attorney, Agent, or Firm*—Sprung Kramer Schaefer & Briscoe

[57] ABSTRACT

The novel compound (2,3-dihydro-5-benzofuranyl)-acetonitrile is prepared by chloromethylating 2,3-dihydrobenzofuran and reacting the resulting 2,3-dihydro-5-chloromethyl-benzofuran with a cyanide. (2,3-Dihydro-5-benzofuranyl)-acetonitrile can be converted by saponification to (2,3-dihydro-5-benzofuranyl)-acetic acid, an important intermediate for the manufacture of various pharmaceutical active substances. This intermediate has hitherto been obtainable only by a laborious procedure and in low yields.

11 Claims, No Drawings

(2,3-DIHYDRO-5-BENZOFURANYL)-ACETONITRILE

The present invention relates to the novel compound (2,3-dihydro-5-benzofuranyl)-acetonitrile, to a process for its preparation and to its use for the preparation of (2,3-dihydro-5-benzofuranyl)-acetic acid, an important intermediate for the manufacture of various pharmaceutical active substances.

The novel compound (2,3-dihydro-5-benzofuranyl)-acetonitrile of the formula (I):

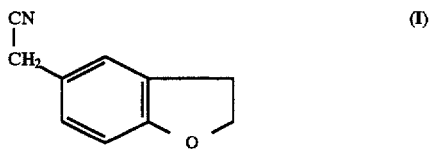

has been found. A process for the preparation of (2,3-dihydro-5-benzofuranyl)-acetonitrile has also been found, said process comprising chloromethylating 2,3-dihydrobenzofuran and reacting the resulting 2,3-dihydro-5-chloromethylbenzofuran with a cyanide to give (2,3-dihydro-5-benzofuranyl)-acetonitrile. The following reaction scheme illustrates the process according to the invention:

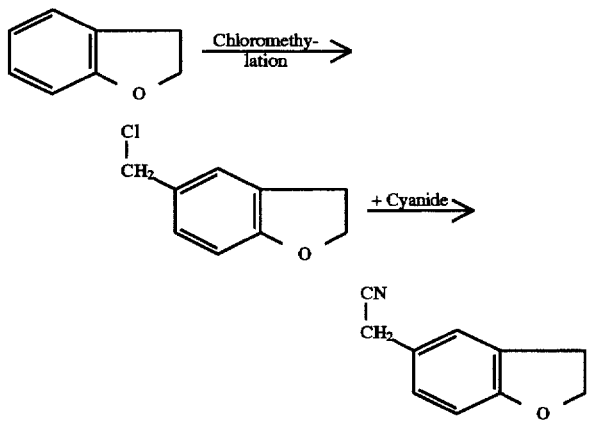

2,3-Dihydro-benzofuran can be obtained for example from phenoxyethanol by cyclizing dehydration (see e.g. J. Am. Chem. Soc. 41, 665 (1919)).

"Chloromethylation" is understood as meaning the introduction of a Cl—$CH_2$ group into a substrate. In the simplest case the substrate is reacted simultaneously with formaldehyde and hydrogen chloride in the presence of a condensation agent. The formaldehyde can be used e.g. as an aqueous solution. It is also possible to use formaldehyde derivatives which release formaldehyde under the reaction conditions, such as formaldehyde condensation products (e.g. 1,3,5-trioxane=paraformaldehyde) and formaldehyde acetals (e.g. dimethylformal, diethylformal, 1,3-dioxane and 1,3-dioxolane). The reaction can also be carried out with special chloromethylating reagents such as α,α'-dichlorodimethyl ether or chloromethyl alkyl ethers of the formula Cl—$CH_2$—O—R, where R is for example $C_1$-$C_{10}$-alkyl. If such special chloromethylating reagents are used, it may be possible to dispense with the addition of hydrogen chloride, although a condensation agent also has to be used in this case.

Examples of suitable condensation agents are Lewis acids and organic and inorganic protonic acids such as zinc chloride, iron chloride, aluminum chloride, tin tetrachloride, sulfuric acid, phosphoric acid and acetic acid.

Based on 1 mol of 2,3-dihydrobenzofuran, the process according to the invention can be carried out using e.g. 1 to 10 mol of formaldehyde or a formaldehyde derivative yielding this amount of formaldehyde, 1 to 10 mol of hydrogen chloride (e.g. gaseous or as an aqueous solution) and 0.02 to 1 mol of condensation agent.

If the reaction is carried out with special chloromethylating reagents (see above), these can be used e.g. in amounts of 1 to 10 mol per mol of 2,3-dihydrobenzofuran, it being unnecessary to add hydrogen chloride.

The chloromethylation can be carried out e.g. without a solvent in excess 2,3-dihydrobenzofuran, although it is also possible to use inert solvents such as water, alcohols, aromatic hydrocarbons or mixtures of said solvents.

The reaction temperatures can be e.g. between −10° and +150° C., preferably between 0° and 100° C. and particularly preferably between 10° and 50° C., depending on the chloromethylating reagent and condensation agent used.

The chloromethylation product, 2,3-dihydro-5-chloromethyl-benzofuran, can be obtained in pure form by conventional methods of working-up, e.g. extraction, distillation of the extraction agent and distillation of the product. For the subsequent reaction with a cyanide, it is generally wholly sufficient to distil the solvent and/or excess 2,3-dihydrobenzofuran and react the resulting crude product with the cyanide.

Examples of suitable cyanides are alkali metal and alkaline earth metal cyanides, cyanides of metals of the first and second subgroups of the periodic table of the elements, and ammonium and phosphonium cyanides. Sodium, potassium, zinc, copper(I) and silver cyanide are preferred, sodium and potassium cyanide being particularly preferred.

The cyanide can be used for example in an amount corresponding to 1 to 5 equivalents of cyanide ions, based on 1 mol of 2,3-dihydro-5-chloromethyl-benzofuran. The amount is preferably 1 to 1.5 equivalents.

The reaction with the cyanide can be carried out e.g. without a solvent in excess 2,3-dihydro-5-chloromethyl-benzofuran. It is preferable, however, to use an inert solvent, optionally mixed with water. Examples of suitable inert organic solvents are alcohols such as methanol, ethanol, propanols and butanols, ketones such as acetone, butan-2-one, methyl isobutyl ketone and cyclohexanone, and sulfur-containing solvents such as dimethyl sulfoxide and tetramethylenesulfone.

The reaction rate can be considerably accelerated by the addition of metal iodides, especially sodium or potassium iodide. It is possible to add for example 0.001 to 0.1 mol of a monovalent iodide, based on one equivalent of cyanide.

The temperatures for the reaction with the cyanide can be e.g. in the range 0° to 200° C. The temperatures are preferably in the range 20° to 150° C. and particularly preferably in the range 40° to 100° C. The reaction can optionally be carried out in an autoclave under pressure, especially when it is desired to work above the boiling point of one of the solvents used.

The reaction with the cyanide is advantageously carried out as far as possible in an anhydrous medium.

The reaction mixture obtained after the reaction with the cyanide can be worked up e.g. by first separating off the precipitated chloride, washing it with a solvent, preferably the one also used in the reaction, combining the filtrates, stripping off the solvents and subjecting the resulting residue to fractional distillation. This generally gives (2,3-dihydro-5-benzofuranyl)-acetonitrile in a yield of over 60% (based on 2,3-dihydrobenzofuran).

(2,3-Dihydro-5-benzofuranyl)-acetonitrile can be converted to the corresponding acid, i.e. (2,3-dihydro-5-benzofuranyl)-acetic acid, by nitrile saponification processes known per se. The saponification can be carried out with substances which give an acid or alkaline reaction, preferably at elevated temperature, in the simplest case by refluxing with aqueous sodium hydroxide solution. The saponification is complete when no more ammonia or ammonium ions are formed. (2,3-Dihydro-5-benzofuranyl) -acetic acid can be isolated from the saponification mixture e.g. by dilution with water, followed by the addition of an acid, e.g. a mineral acid, and filtration of the (2,3-dihydro-5-benzofuranyl)-acetic acid which then precipitates out.

(2,3-Dihydro-5-benzofuranyl)-acetic acid can thus generally be obtained in yields of over 85% (based on the nitrile).

(2,3-Dihydro-5-benzofuranyl)-acetic acid is an important intermediate for the manufacture of pharmaceuticals which act as inflammation inhibitors (see J. Med. Chem. 29, 2326–2329 (1986)), analgesics and antipyretics (see EP-A 132 130), antimuscarinergic agents (see EP-A 388 054) and antibacterials (see U.S. Pat. No. 4,138,971). The route described here for the preparation of (2,3-dihydro-5-benzofuranyl)-acetic acid via the novel compound (2,3-dihydro-5-benzofuranyl)-acetonitrile represents by far the shortest and most efficient route for the preparation of (2,3-dihydro-5-benzofuranyl)-acetic acid.

The known processes for the preparation of (2,3-dihydro-5-benzofuranyl)-acetic acid are multistage processes (see U.S. Pat. No. 4,138,971) and/or only give the desired product in unsatisfactory yields. Thus the route via the Willgerodt reaction (ketone+ammonium polysulfide→acid amide→acid) only gives total yields of less than 40% and proceeds via intensely odorous sulfur compounds (see J. Med. Chem. 29, 2326–2329 (1986) and EP-A 132 130).

EXAMPLES

Example 1

120.2 g of 2,3-dihydrobenzofuran were dissolved in 500 ml of benzene and cooled to 0° C. With external cooling, this solution was saturated with hydrogen chloride gas. With vigorous stirring, 40 g of paraformaldehyde were then introduced in such a way that the internal temperature could be kept below 25° C. The introduction of hydrogen chloride gas was continued simultaneously. When the addition of paraformaldehyde was complete, the introduction of hydrogen chloride gas was continued for one hour at 10° C. and the mixture was subsequently stirred for a further hour at room temperature. The sediment formed was then separated off by decantation, the benzene solution was neutralized with solid sodium hydrogen carbonate and the benzene was distilled off.

The residue was dissolved in 500 ml of dry acetone and 74 g of dry sodium cyanide and 5 g of sodium iodide were added. The mixture was refluxed for 16 hours, with stirring and with the exclusion of moisture, and cooled, the sodium chloride which had precipitated out was filtered off and washed with 250 ml of acetone and the solvent was stripped off from the combined filtrates. The residue was worked up by fractional distillation under vacuum. The fraction with a boiling point of 145°–152° C. at 1.3 mbar was collected and analyzed. 101 g (97.5%) of (2,3-dihydro-5-benzofuranyl)-acetonitrile were thus obtained, corresponding to a yield of 61.9% of theory.

$^1$H NMR spectrum: 3.2 ppm (t, 2 H); 3.65 ppm (s, 2H); 4.6 ppm (2 H); 6.75 ppm (d, 1 H); 7.0 ppm (2d, 1 H) and 7.1 ppm (broad s, 1 H).

Example 2

95.6 g of the (2,3-dihydro-5-benzofuranyl)-acetonitrile obtained according to Example 1 and 192 g of 25% by weight sodium hydroxide solution were refluxed for 3 hours. After ca. 2 hours the initially two-phase mixture became homogeneous. When the evolution of ammonia had ended (after about 3 hours), the mixture was cooled and diluted with 300 ml of water and the carboxylic acid formed was precipitated out with 61.5 g of sulfuric acid (96% by weight). After cooling, filtration, washing (with 3 times 100 ml of water) and drying, 101 g of (2,3-dihydro-5-benzofuranyl)-acetic acid melting at 96°–98° C. were obtained with a purity of 98.5%, corresponding to a yield of 93% of theory.

The (2,3-dihydro-5-benzofuranyl)-acetic acid prepared in this way gave the following $^1$H NMR spectrum: 3.1 ppm (t, 2 H); 3.6 ppm (s, 2 H); 4.5 ppm (t, 2 H); 6.7 ppm (d, 1 H); 7.0 ppm (d, 1 H); 7.1 ppm (s, 1 H).

This material was found to be identical to (2,3-dihydro-5-benzofuranyl)-acetic acid which had been obtained according to EP-A 132 130 (see Preparations 11–13 therein).

What is claimed is:

1. (2,3-Dihydro-5-benzofuranyl)-acetonitrile of the formula

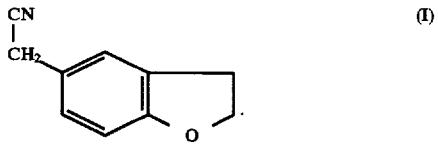

2. A process for the preparation of (2,3-dihydro-5-benzofuranyl)-acetonitrile, which comprises chloromethylating 2,3-dihydro-benzofuran and reacting the resulting 2,3-dihydro-5-chloromethyl-benzofuran with a cyanide to give (2,3 -dihydro-5-benzofuranyl)-acetonitrile.

3. The process as claimed in claim 2 wherein the chloromethylation is carried out using formaldehyde or a formaldehyde derivative which releases formaldehyde under the reaction conditions, hydrogen chloride and a condensation agent.

4. The process as claimed in claim 2 wherein the chloromethylation is carried out using α,α'-dichlorodimethyl ether or a chloromethyl alkyl ether of the formula Cl—CH$_2$—O—R, where R=C$_1$-C$_{10}$-alkyl.

5. The process as claimed in claim 2, wherein the condensation agent is selected from the group consisting of Lewis acids and organic and inorganic protonic acids.

6. The process as claimed in claim 2 wherein 1 to 10 mol of formaldehyde or a formaldehyde derivative which yields this amount of formaldehyde, 1 to 10 mol of hydrogen chloride and 0.02 to 1 mol of condensation agent are used per mol of 2,3-dihydro-benzofuran.

7. The process as claimed in claim 2 wherein the chloromethylation is carried out at between −10° and +150° C.

8. The process as claimed in claim 2 wherein the cyanide is selected from the group consisting of alkali metal and alkaline earth metal cyanides, cyanides of metals of the first and second subgroups of the periodic table of the elements and ammonium and phosphonium cyanide.

9. The process as claimed in claim 2 wherein a metal iodide is added to the reaction with the cyanide.

10. The process as claimed in claim 2 wherein the reaction with the cyanide is carried out at 0° to 200° C.

11. A process for the preparation of (2,3-dihydro-5-benzofuranyl)-acetic acid which comprises saponifying (2,3-dihydro-5-benzofuranyl)-acetonitrile.

* * * * *